United States Patent [19]

Schneider et al.

[11] Patent Number: 5,532,770
[45] Date of Patent: Jul. 2, 1996

[54] APPARATUS AND METHODS FOR EVALUATING VISION THROUGH AN INTRAOCULAR LENS

[76] Inventors: Richard T. Schneider, 17 Alachua Highlands, Alachua, Fla. 32615; Richard H. Keates, 71 Whitman Ct., Irvine, Calif. 92715

[21] Appl. No.: 423,104

[22] Filed: Apr. 18, 1995

[51] Int. Cl.⁶ .............................. A61B 3/10; A61B 3/00
[52] U.S. Cl. ............................................ 351/205; 351/246
[58] Field of Search .................................... 351/200, 205, 351/246; 623/6

[56] References Cited

U.S. PATENT DOCUMENTS

| | | | |
|---|---|---|---|
| 4,927,260 | 5/1990 | Gordon | 351/205 |
| 5,192,318 | 3/1993 | Schneider et al. | 623/6 |

*Primary Examiner*—William L. Sikes
*Assistant Examiner*—Huy Mai
*Attorney, Agent, or Firm*—Merchant, Gould, Smith, Edell, Welter & Schmidt

[57] ABSTRACT

The invention includes apparatus and methods for evaluating vision through an intraocular lens. An image passes through a cornea, an intraocular lens, and a fovea window that are in a collinear array. In addition, the apparatus can include a human eye model, a fovea projector, and readable targets. The apparatus can be used to evaluate the vision of a subject through an intraocular lens such as a monofocal or bifocal intraocular lens. The ability of the subject to focus on one or more images at the fovea window provides information for evaluation of the subject's ability to see through an intraocular lens. Through movement of the fovea window or the intraocular lens dimensions or geometric constants of the subject's eye can be determined.

14 Claims, 4 Drawing Sheets

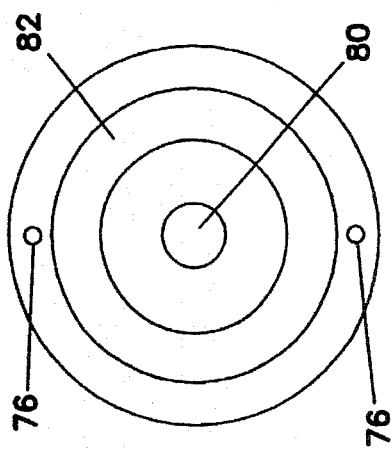
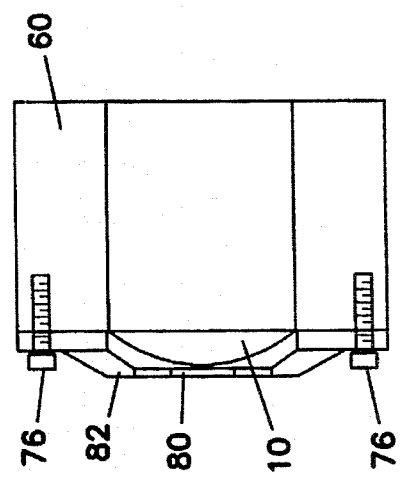
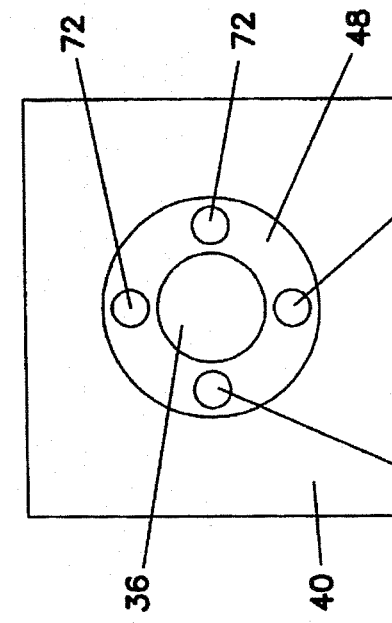
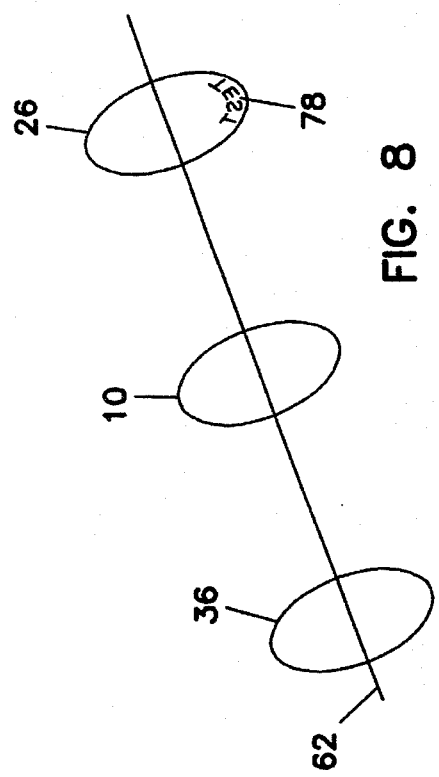
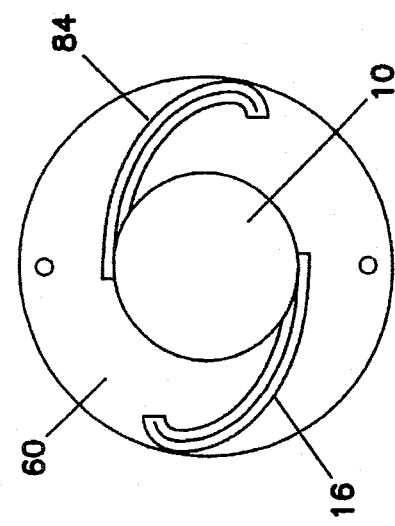

APPARATUS AND METHODS FOR EVALUATING VISION THROUGH AN INTRAOCULAR LENS

FIELD OF THE INVENTION

This invention relates generally to apparatus and methods for use in simulating vision through a patient's eye and for use in testing a patient's suitability for a selected intraocular lens (IOL).

BACKGROUND OF THE INVENTION

Intraocular lenses are used as artificial lens implants in eyes from which the natural lens has been removed. A natural lens changes its focal length by deformation, known as accommodation, to provide a focused image. An IOL does not focus in this manner. Monofocal IOLs provide focused vision at only a single distance range. If the focal length is selected to provide a sharp image for a distant object, then an object which is closer, for example at reading distance, will not be sharply focused on the retina. It is possible to sharply image closer objects by selecting a different focal length, but then distant objects would appear out of focus.

Bifocal IOLs are advantageous for providing clear vision at two distance ranges. U.S. Pat. No. 5,192,318, issued Mar. 9, 1993, the disclosure of which is incorporated by reference, concerns various bifocal IOL constructions. A bifocal IOL produces two superimposed images with one image always out of focus. Not all people can select between the two images and process the focused image sufficiently to see. Prior to surgery to implant a bifocal IOL in a patient, it is desirable to assure that the patient is a good candidate for a bifocal IOL. Implantation surgery carries inherent risks to the health of the patient, as with any surgery. Additional eye surgery can also damage the eye and compromise the quality of vision after surgery. Removal of an unsatisfactory lens and replacement with a new lens subjects the patient to further risk to vision and health which may be viewed as unacceptable to both the health care professional and the patient.

Thus, there is a need for an apparatus and method for testing the ability of a subject to see properly using a bifocal IOL. In addition, there is a need for an apparatus and method to compare a subject's vision through different types of IOLs. Another need in the vision care community is an apparatus and method to monitor over months or years the geometrical and refractive configuration of an eye. The apparatus and methods of the current invention address these needs.

SUMMARY OF THE INVENTION

The invention includes apparatus and methods for evaluating vision through an IOL. A preferred apparatus includes a human eye model having a basin or container that can hold liquid. Another component of the human eye model is a device that holds an IOL in the basin so that the IOL can be positioned to mimic the geometry and other characteristics of an eye. The human eye model also includes a cornea through which light enters the human eye model. The cornea is a lens that covers an aperture in the human eye model. The cornea can mimic the shape and optical properties of the cornea of an eye. Light enters the human eye model through the cornea, passes through the IOL, and then passes through a fovea window. The cornea, IOL, and fovea window form a collinear array whose distances can mimic the corresponding distances in the subject's eye.

The apparatus for evaluating vision through an IOL can include additional components as well. The IOL is mounted in an IOL holder. The IOL holder can include an iris cap that mimics the iris of an eye. The IOL holder can be mounted on a control mechanism such that it is moveable relative to the basin of the eye model or the cornea. The control mechanism can be mounted on a removable lid that allows ready access to the IOL in the IOL holder for changing the IOL. The cornea can be mounted on a cornea holder that forms a liquid tight seal over the aperture in the human eye model and that allows interchangeable corneas. The apparatus can also include a selection of corneas or iris caps that can be interchanged to more closely model the subject's eye. Furthermore, a selection of IOLs can be included so that the subject's tolerance of various designs of IOLs can be tested.

The human eye model can be mounted on a fovea projector. A fovea projector includes a fovea window that can be moved relative to the IOL. The fovea projector also includes an objective lens and an eyepiece that are oriented so that light entering the fovea projector through the fovea window is detectable at the eyepiece. The fovea window can fit in an aperture in the human eye model.

A method of the invention uses an apparatus simulating an eye to evaluate a subject's vision through an IOL. The method includes having a subject view symbols mounted on or near the fovea window such that these symbols are focused in the subject's vision. Then, the subject, looking through the eyepiece of the fovea projector, views sequentially one or more targets that can be at different distances from the human eye model. The subject's ability to view the targets is evaluated.

When a bifocal IOL is mounted in the human eye model, the subject's suitability for implantation of a bifocal IOL can be evaluated. A subject that is unable to view through a bifocal IOL targets at different distances corresponding to the different powers of the lens would be unsuitable for implantation of a bifocal IOL. Alternatively, IOLs of different design may be inserted in the human eye model and the subject's vision through the different IOLs can be evaluated. The IOLs can be moved, tilted, or decentered relative to the cornea or fovea window in this procedure. This allows selection of the design of IOL most suitable for the subject. In addition, through movement of the fovea window or the IOL relative to the cornea or the basin of the human eye model, dimensions or geometric constants of the subject's eye can be determined.

The method can require optimization of the position or characteristics of different components of the human eye model. The method can include changing the position of the IOL relative to the cornea or the fovea window. This can allow evaluation of the subject's vision at different geometric configurations. The method can also include evaluating the subject's vision with different iris caps or different corneas installed in the human eye model. In addition, the method can involve altering the distance between the fovea window and the IOL or the cornea.

The apparatus and methods of the invention can also include uses in model systems and for teaching. The image from the fovea window can be projected onto a screen or film, into a video display system, or other storage or display device. The image from the fovea window can be projected into the eye of a nonhuman animal. The methods and apparatus can be used for training users, for teaching vision care professionals, for clinical or pharmacological studies, for research, and the like.

BRIEF DESCRIPTION OF THE DRAWINGS

FIG. 4 is an enlarged front view of the cornea holder with the cornea in place.

FIG. 5 is an enlarged cross-sectional side view of the IOL holder with the attached iris cap and the IOL in place.

FIG. 6 is an enlarged front view of the IOL holder with the iris cap in place.

FIG. 7 is an enlarged front view of the IOL holder with the iris cap removed and the IOL in place.

FIG. 8 is a perspective schematic view of the cornea, the IOL, and the fovea window.

DETAILED DESCRIPTION OF THE INVENTION

Figure 1:
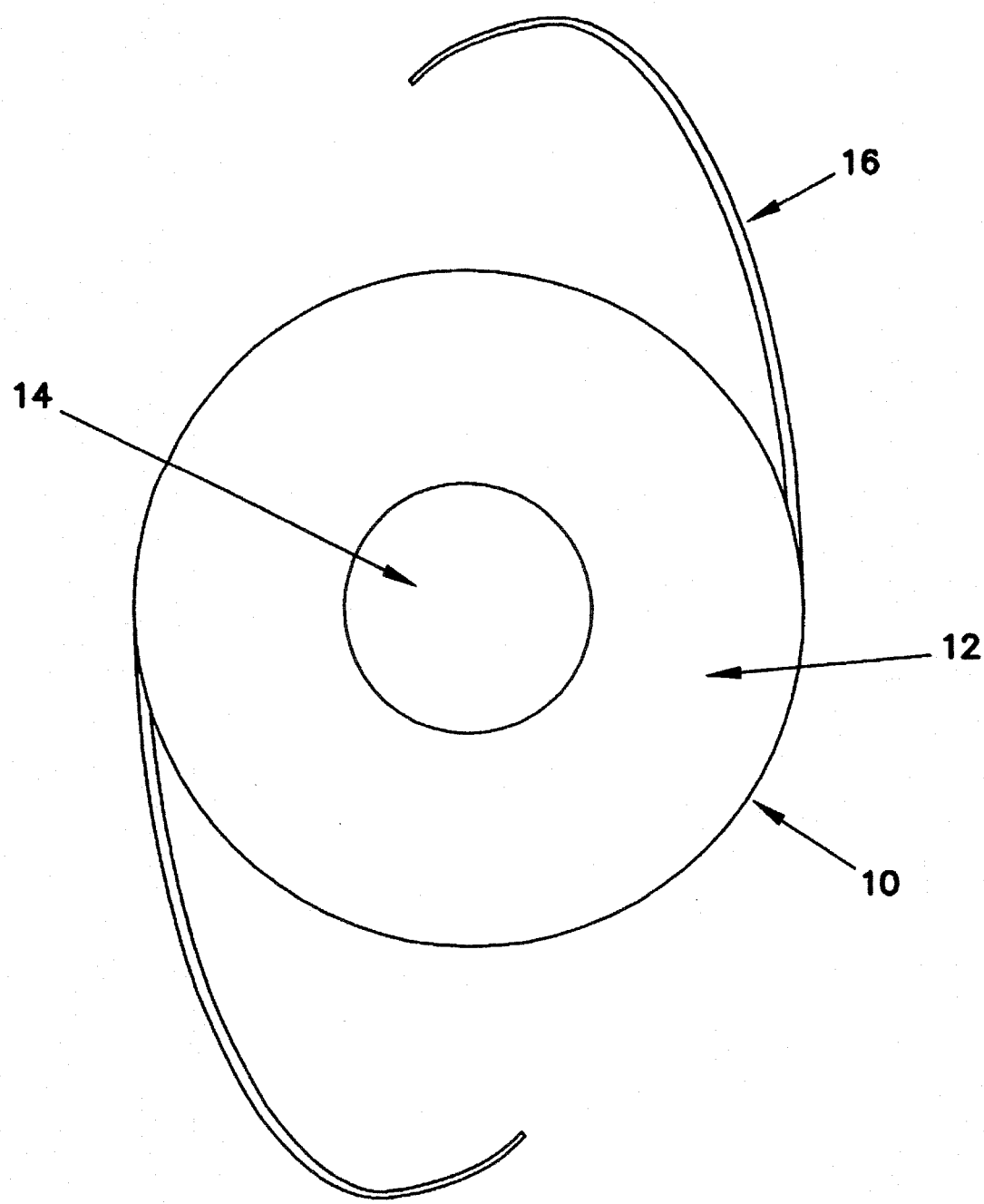
FIG. 1 is a front plan view of a coaxial bifocal IOL.

Referring now to FIG. 1, a bifocal IOL 10 has two lens portions 12, 14 of different focal lengths. Typically, bifocal IOLs have concentric lens portions with, for example, an outer annular portion 12 of one optical power and an inner circular portion 14 of another optical power. Thus, two images, one in focus and the other out of focus are projected simultaneously upon the retina. The subject's brain is then required to select and process the focused image. Unfortunately, not every person is capable of selecting the focused image, so it is desireable or necessary to test for this ability before implanting a bifocal IOL 10. Haptic members 16 project outward from the bifocal IOL 10 to allow for attachment of the bifocal IOL in the patient's eye.

Bifocal IOL 10 has properties that facilitate proper evaluation of the focused image in many people. Such an IOL typically has an inner, reading lens less than 2 mm in diameter with a difference between the power of the two lenses of at least about 3.0 diopters (D) but advantageously at least about 3.5 D. The difference in power enables the brain to more easily accomplish the image evaluation. There are configurations for bifocal IOL's other than the one shown in FIG. 1. For example, a circular lens divided into two halves along the diameter is feasible or a lens with more than two rings is possible. In all cases, there must be a substantial difference in the amount of focusing between two competing images, such as at least about 3.0 D. However, this will be different for different patients.

Figure 2:
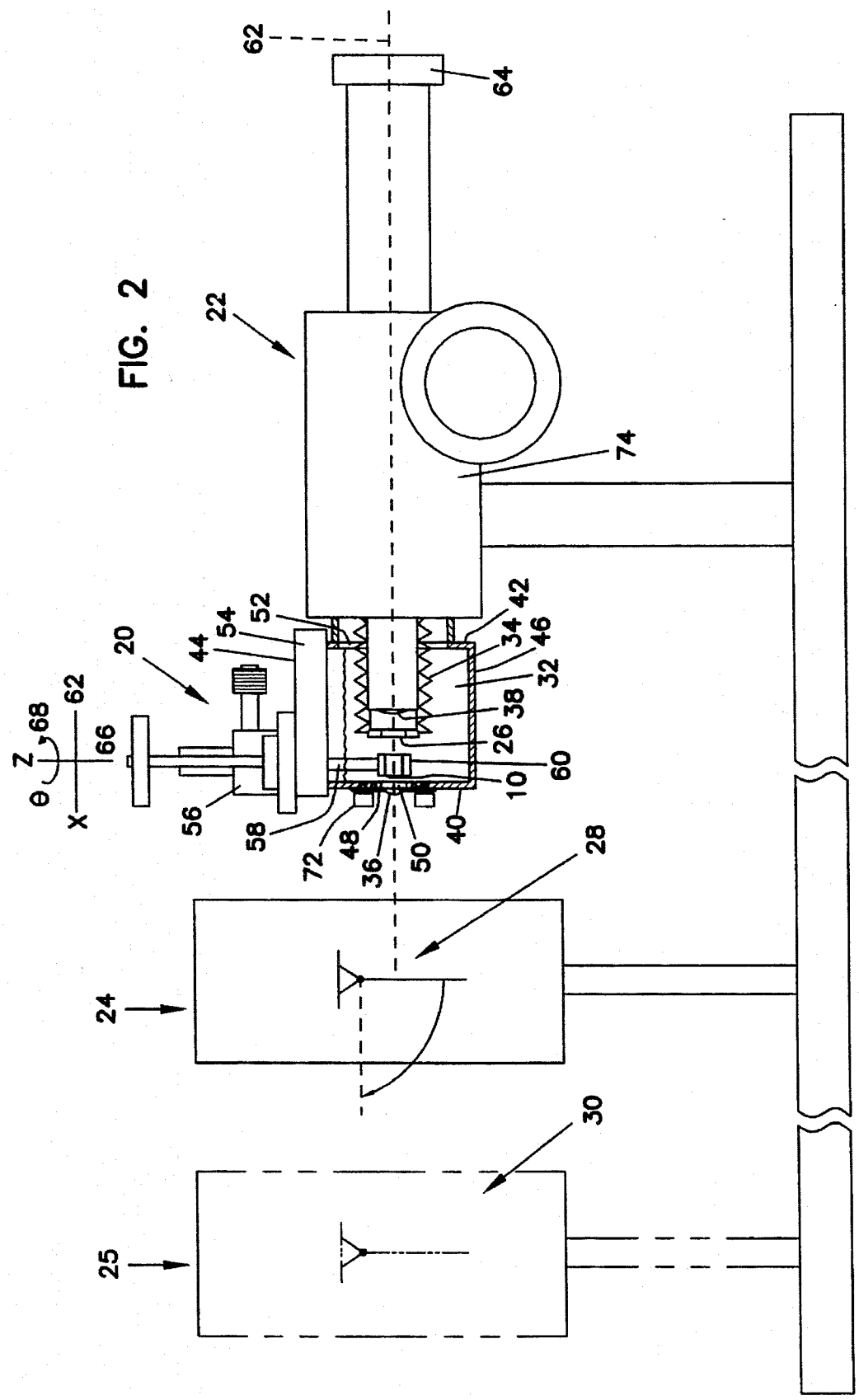
FIG. 2 is a side view of an embodiment of an IOL evaluation apparatus according to the present invention.

Bifocal IOL 10 can be mounted in an IOL evaluation apparatus 18 shown in FIG. 2. FIG. 2 shows IOL evaluation apparatus 18, which includes a human eye model 20, a fovea projector 22, and one or more target boxes 24. Human eye model 20 is shown attached to fovea projector 22. A function of fovea projector 22 is to project an image appearing at fovea window 26 of human eye model 20 onto the fovea of the observer at a 1:1 imaging ratio. The patient will observe either a target 28 for reading vision or a target 30 for distance vision. Provisions are, optionally and advantageously, made that reading target 28 can be removed and reinserted with a minimum time delay.

Figure 3:
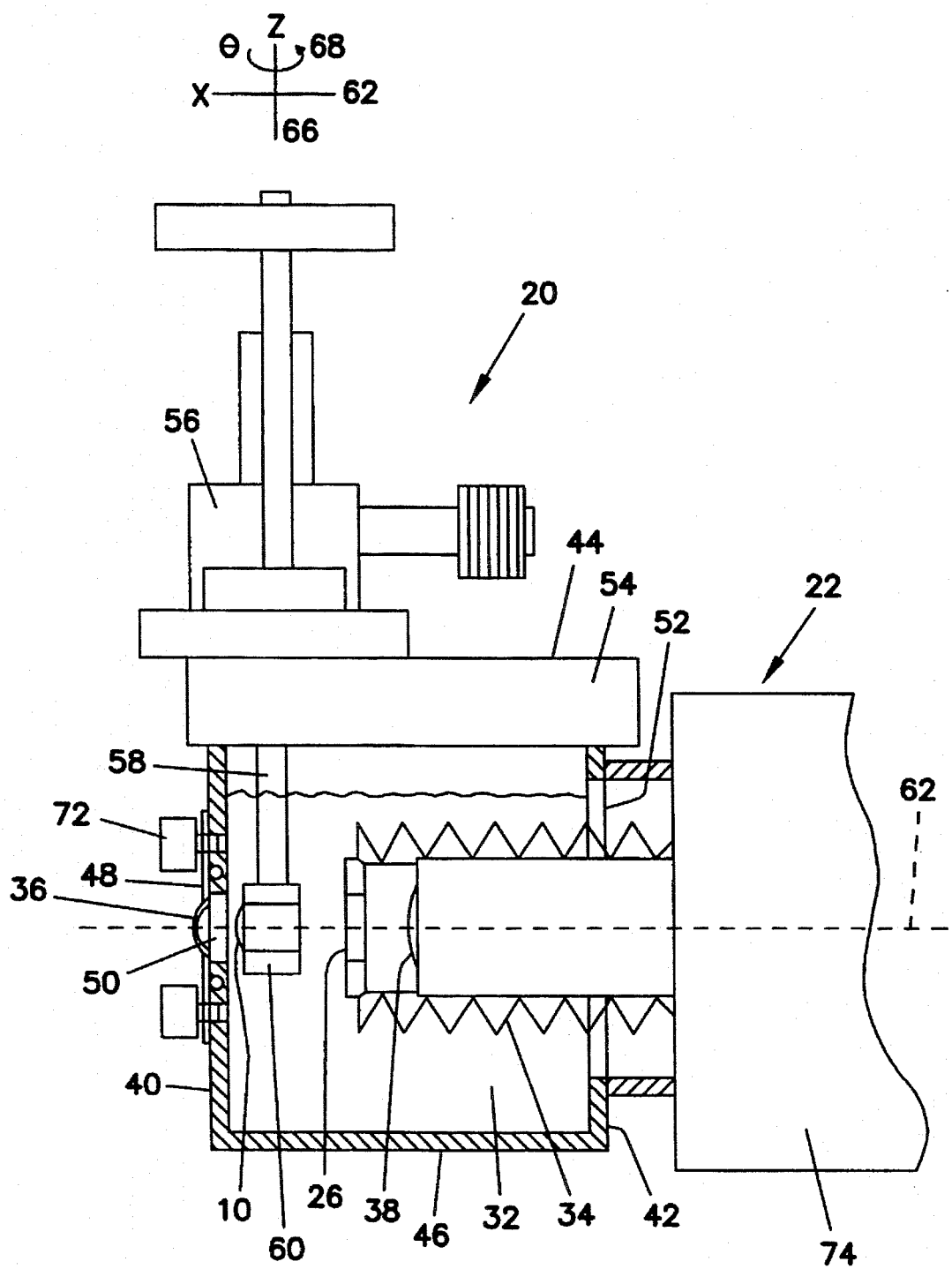
FIG. 3 is an enlarged cross-sectional side view of the human eye model mounted on the fovea projector as part of the IOL evaluation apparatus of FIG. 2.

FIG. 3 shows an enlarged view of human eye model 20. Human eye model 20 includes a basin, or other container or enclosure, 32, typically about 4 cm long, that can be advantageously filled with saline solution, preferably, having the same refractive index as the human vitreous. Seal to the outside is provided by bellows 34 and fovea window 26. In a preferred embodiment, bellows 34 allows adjustable placement of fovea window 26 at any location from about 9 mm to about 40 mm from the surface of human eye model cornea 36. The distance between fovea window 26 and objective lens 38 of fovea projector 22 is kept constant, even if fovea window 26 is moved.

Human eye model 20 is capable of mounting detachably on a fovea projector 22. Fovea window 26 protrudes into human eye model 20 with a seal between fovea projector 22 and human eye model 20 that retains water or other fluids in the basin 32 of the human eye model 20. Basin 32 of human eye model 20 can contain liquid and has several sides. The embodiment illustrated in FIG. 3 includes sides 40, 42, 44, and 46, but basin 32 may include additional sides or configurations.

A cornea holder 48 is mounted over an aperture 50 in side 40. Cornea holder 48 seals aperture 50 so that basin 32 can hold liquid above the level of aperture 50. Opposite from side 40, and typically about 4 cm from side 40, is side 42. Side 42 includes an aperture 52 that receives fovea window 26 of fovea projector 22 and bellows 34 or other mechanism that seals fovea projector 22 and fovea window 26 in aperture 52 such that the seal is liquid tight. Side 44 is adjacent to side 40 and in a preferred embodiment includes a removable lid 54. Side 44 also includes a control mechanism 56 that controls the position of IOL holder 60 and a stem 58 that links control mechanism 56 and IOL holder 60. Stem 58 projects into basin 32 and supports IOL holder 60, typically at one end of stem 58.

When human eye model 20 is mounted on fovea projector 22 as shown in FIG. 3 and control mechanism 56 is adjusted appropriately, the following components of human eye model 20 are in a collinear configuration: cornea 36 in the cornea holder 48, an IOL in IOL holder 60, and fovea window 26. This collinear configuration defines an x-axis 62. Typically, fovea window 26 and eyepiece 64 of fovea projector 22 are also on x-axis 62. Alternatively, the light path from fovea window 26 to eyepiece 64 of fovea projector 22 is not linear but instead is formed using one or more prisms, mirrors, or lenses such that light that enters through cornea 36 forms an image that can be seen through eyepiece 64 of fovea projector. When control mechanism 56 is adjusted appropriately, IOL holder 60 is between cornea 36 and fovea window 26. Measurements of dimensions of the human eye model are typically made using as a reference point the convex apex of cornea 36 as 0 mm. From this reference point in a typical version of the human eye model, cornea 36 meets cornea holder 48 at about 0.6 mm, IOL holder 60 is at about 5.6 mm, and fovea window 26, which is continuously adjustable in position over a wide range, is at about 24.0 mm Control mechanism 56 is mounted on side 44 (as shown in FIG. 3) in a manner such that it can controllably move stem 58 relative to side 44 and basin 32 to control the position of IOL holder 60. Control mechanism 56 anchors and manipulates stem 58. Stem 58 also is linked to IOL holder 60. Advantageously, control mechanism 56 controllably positions IOL holder 60 and stem 58 along x-axis 62 from cornea 36 to fovea window 26, along z-axis 66 perpendicular to both x-axis 62 and side 44, rotationally about z-axis 66 at an angle theta 68, and optionally along a y-axis 70, which is perpendicular to both x-axis 62 and z-axis 66. In a preferred embodiment of the invention, control mechanism 56 is mounted on a lid 54 to basin 32 of eye model 20. In this case, insertion of IOL 10 is easily accomplished by removing lid 54 including control mechanism 56 from eye model basin 32. The position of lid 54 can be reproducibly set by a mechanism that assures that lid 54 sits in only one location, such as locator pins on the basin.

FIG. 5 shows a cross-sectional side view of IOL holder 60. IOL holder 60 mounts, preferably detachably, on stem 58. An IOL in IOL holder 60 can be positioned between cornea 36 and fovea window 26 allowing light to project through cornea 36, an IOL in IOL holder 60, and fovea window 26. IOL holder 60 allows for secure positioning of IOL 10 in IOL holder 60. In a preferred embodiment, haptic members 16 of IOL 10 are positioned in recessed areas 84 of IOL holder 60, as shown in FIG. 7.

IOL holder 60, optionally, includes an arrangement for mounting an iris cap 82 adjacent to IOL 10. The mounting arrangement as shown in FIGS. 5 and 6 includes threaded, screw-like fasteners 76 that fasten iris cap 82 to IOL holder 60, but other fasteners will work as well. Iris cap 82 provides an aperture 80 through which light can pass that is of smaller diameter than the IOL 10 (FIG. 5). This mimics the structure of the human eye in which a variable iris is smaller than the lens. The mechanical iris of the human eye model need not be adjustable since detachable iris caps 82 with different sized apertures can be interchanged on IOL holder 60. However, an adjustable iris cap may be used.

Preferably, IOL holder 60 can be moved along x-axis 62, z-axis 66 and, optionally, y-axis 70, as well as rotated about angle theta 68. Displacement along x-axis 62 is used to position IOL 10 the proper distance from cornea 36. Movement along z-axis 66 and, optionally, y-axis 70 mimics decentering of the lens. Movement through theta angle 68 simulates tilt. All of these manipulations can be accomplished while IOL 10 is submerged or in place and the patient is observing. The settings of the manipulators can be sensed by standard optical encoders or other sensors. Optical encoders sense the position of the IOL or the setting of control mechanism 56. The position settings are then fed into a computer for recording and analysis, advantageously, along with other data for the patient.

Light enters human eye model 20 through aperture 50 in side 40. During use, human eye model 20 is filled with liquid above aperture 50 in side 40, so aperture 50 must be covered or filled with transparent material that forms a liquid tight barrier with side 40 of human eye model 20. For example, aperture 50 could be filled with a transparent plastic or glass plug. Alternatively, a lens could be fitted in or over aperture 50 with an appropriate apparatus for forming a seal around the aperture.

In a preferred embodiment of the invention, aperture 50 is sealed by a cornea 36 in a cornea holder 48. Cornea holder 48 and cornea 36 are shown attached to human eye model 20 in FIG. 3. A front view of cornea holder 48 and cornea 36 on basin 32 of human eye model 20 is shown in FIG. 4.

Cornea holder 48 mounts on side 40 of human eye model basin 32. Cornea holder 48 mounts over aperture 50 of basin 32 that allows light to enter the basin 32 along x-axis 62. Cornea holder 48 includes fasteners 72 that attach cornea holder 48 to basin 32 of human eye model 20. When mounted, cornea holder 48 forms a liquid-tight junction with basin 32 so that basin 32 retains liquid. Preferably, cornea 36 and cornea holder 48 combine to form a convex surface approximating the surface of an eye.

Cornea 36 is a lens which preferably approximates optical properties of the cornea of the subject's eye or of a typical eye. Preferably, cornea 36 also approximates the shape of a cornea of a human eye. Cornea 36 is easily removed from and replaced in cornea holder 48. Corneas 36 having different optical powers and different astigmatic afflictions are included in the invention. Such corneas 36 can be supplied as a set that facilitates practicing the method of this invention. Typically, the shape of the patient's cornea is known prior to using the invention.

Fovea projector 22 produces an enlarged (between about 10 x and about 20 x) rear image which is observed by the patient through an eyepiece 64. Fovea projector 22 includes in a collinear array fovea window 26, objective lens 38, and eyepiece 64. An image or light entering through fovea window 26 passes through objective lens 38 to eyepiece 64 where it can be perceived or detected. Alternatively, fovea window 26, objective lens 38 and eyepiece 64 are not in a linear array, but light is guided between them by one or more prisms, mirrors, or lenses. Components of the fovea projector are supported by fovea projector body 74. Fovea projector body 74 is opaque and light tight such that movement of fovea window 26 or eyepiece 64 relative to the rest of fovea projector body 74 occurs without light entering fovea projector body 74 other than through eyepiece 64 or fovea window 26. Fovea projector 22 can be mounted on a device that allows it to be moved vertically and horizontally.

Fovea window 26 has small letters or symbols 78 engraved or otherwise mounted or supported on its surface, preferably the anterior surface. Advantageously, the letters are engraved on the anterior surface. Preferably, letters or symbols 78 can be illuminated, preferably when the view of the target is blocked.

Movement of fovea window 26 relative to eye model 20 or fovea projector body 74 can be accomplished by a variety of methods including sliding as in a simple telescope, a screw and gear system, or other positioning apparatus such as is used in a microscope, a telescope, binoculars, or another optical device. The positioning apparatus and fovea projector body 74 optionally detects and relays the position of the fovea projector window to an external recording device.

Target 28 is, typically, positioned at standard reading distance from human eye model 20 and fovea window 26. It is positioned along x-axis 62 that extends from fovea projector eyepiece 64 through human eye model 20. Readable target 28 can be of any type commonly used in testing vision. Preferably, target 28 is mounted in target box 24. Target box 24 supports target 28 and, advantageously, allows target 28 to be quickly and easily removed from the imaging field of human eye model 20. For example, target 28 can be rapidly flipped upward out of the imaging field. Moving target 28 allows a viewer at fovea projector eyepiece 64 to see through target box 24 to target 30 at greater distance. The apparatus can, optionally, include target 30 and, possibly, target box 24 about twenty feet from the human eye model. Then the apparatus can test vision at a greater distance.

Both target boxes 24 and 25 may, optionally, include a lighting system for illuminating the target. In addition, targets 28, 30 or target boxes 24, 25 can include an apparatus that allows the position of the target or target box to be adjusted both horizontally and vertically.

The apparatus can include human eye model 20 mounted on fovea projector 22 so that cornea 36, IOL holder 60, and fovea window 26 are in a collinear array. Through fovea projector eyepiece 64 a subject can view target 28 at reading distance and a target for distance viewing 30 as well. To use the apparatus for evaluating an IOL, an IOL 10 is mounted in IOL holder 60 and control mechanism 56 is used to adjust the position of IOL 10 between fovea window 26 and cornea 36.

The apparatus described above is useful since prior to surgery to implant an IOL it is desirable, even necessary, to evaluate a patient's ability to process the focused image from a bifocal IOL 10. The invention includes methods to accomplish such evaluation. Evaluation, preferably, is done years before a patient requires cataract surgery while the patient's vision is still good. Screening would be repeated until the surgery becomes necessary. This screening would allow the ophthalmologist to recommend implanting a bifocal IOL or another IOL. It is important to screen out patients that cannot handle a bifocal IOL, since in such cases an implanted bifocal IOL may have to be removed. This repetitive eye surgery is potentially damaging and undesirable.

Usually both eyes do not become afflicted with cataract at the same time. In cases when surgery becomes necessary without having prior yearly screenings performed, it is therefore sufficient to use the eye that is not yet afflicted by cataract for testing the patient's compatibility for a bifocal IOL. This is possible since actually the brain is tested rather than the eye.

The screening method, like a bifocal IOL, produces two superimposed images in the patient's eye, one for reading and the other for distance vision. As with an implanted IOL, one image is always out of focus. The image evaluation system of the brain will try to select the focused image. Unfortunately, not all people are alike and the brains of some patients cannot produce the correct evaluation of the focused image. These patients then experience double lines instead of edges.

While an important concern is to screen patients to ensure that a bifocal implant is appropriate for them, screening can also allow the ophthalmologist to compare lenses of different design and different make to be able to give the best advice to his/her patients. This is significant, since without such screening the patient and physician have no method to determine the lens most suitable for implantation. Currently, only after implantation can the physician test for acuity or interview the patient about poor color performance or lens aberrations. However, after implantation any remedial steps require additional and potentially damaging eye surgery.

Furthermore, the medical community should find it useful to record the changes in the geometrical and refractive configuration of the patient's eye over the lifetime of the patient. The present invention can be sufficiently automated to produce records of this kind within a few minutes. In this case, it can be used for all patients regardless of whether or not a bifocal implant is anticipated. Such an apparatus and method are required to gather more information about the subject's vision than can currently be obtained from tests and patient interviews. This apparatus and method can then increase the success rate for implantation of bifocal IOLs.

A method of the invention includes various steps described in the following paragraphs. In carrying out this method, it is assumed that the geometrical dimensions of the patient's eye are known. Then, for example, the distance between IOL 10 and fovea window 26 are set to equal this distance. However, for many purposes a typical or average distance may be chosen. For other purposes the geometry of the patient's eye can be determined by standard methods.

The subject must be able to focus on fovea window 26. The fovea window 26 is illuminated from the outside by a suitable light source, while the view of target 28 is blocked, for example, by a suitable shield. Fovea window 26 has small letters or other symbols or images 78 on or near its surface. The letters, symbols, or images 78 are preferably engraved on fovea window 26 but they can be mounted or supported on or near the surface of the fovea window. The size of letters, symbols, or images 78 are chosen to be the smallest size the subject can be expected to read or discern. The subject is asked to manipulate fovea projector eye piece 64 distance until they can read letters, symbols, or images 78 on fovea window 26. After this is accomplished, fovea window 26 and IOL holder 60 are placed at a distance believed to represent the corresponding distance in the subject's eye.

For evaluating suitability of a bifocal IOL 10 the following is carried out. The subject is asked to read the reading target 28. If the subject is no longer capable of accommodation, the subject's eye is still focused on the anterior side of fovea window 26. The subject's eye will, therefore, relay in a 1:1 relationship to their own fovea whatever appears on the fovea window. If the subject is capable of selecting the focused image they can read reading target 28 properly. Next, distance vision can be tested. To test distance vision, reading target 28 is temporarily removed and the subject is asked to read the distance target 30. Alternatively, the subject can first read the distance target 30, then reading target 28 is inserted in the patient's field of view.

Under these conditions the subject is exposed to two superimposed images stemming from two lenses of bifocal IOL 10, one of these images being unfocused and the other focused. If the subject can accommodate, their brain can select the focused image. If the subject can read the target shown second, it is proper to conclude that the bifocal IOL can be successfully implanted.

If the subject cannot read one or both of the targets properly, fovea window 26 was, possibly, not placed in the proper location. Therefore, if an improvement in the subject's vision can be made by moving fovea window 26, the geometrical constants of the subject's eye should be remeasured. Another possibility is that the distance from cornea 36 to IOL 10 is incorrect. In this case, movement of IOL 10 along x-axis 62 should provide improvement. Still another possibility is that an inappropriate cornea 36 was selected. That can be checked by replacing cornea 36 with a slightly different one, for example cornea 36 of a slightly different power or shape.

A main concern, of course, is that IOL 10 may be properly selected. The design of the simulator sees to it that it is convenient to remove and insert IOLs 10 in the IOL holder 60. In a preferred embodiment of the invention, this can be accomplished by removing lid 54 including control mechanism 56 from eye model basin 32, inserting a different IOL 10, and reinserting the assembly. Locator pins ensure that the lid is placed in the same location as it was before, in this preferred embodiment. A variety of IOLs can be tested until a satisfactory match is found between subject and IOL.

When an apparently suitable IOL 10 has been selected the subject's tolerance to the geometry of the implant can be tested. For example, the operator can decenter IOL 10 until the subject can no longer perform at both distance vision and reading vision. Decentering includes displacement along z-axis 66 and y-axis 70. Also, rotation through angle theta 68 can explore how much tolerance for tilt exists. Obviously, tolerance for all the mentioned displacements will be different for different patients and different lens designs. If there is an indication that only small tolerance exists for any of these displacements, the operator may want to test the patient on a monofocal implant, to determine if better tolerance exists. This enables the vision professional to form a well rounded professional opinion as to what kind of implant he should prescribe for the patient. Once a satisfactory match between subject and IOL has been achieved and the vision professional is satisfied that the geometrical constants of the patient's eye have been properly simulated, the prescription of the IOL can be certified.

An ophthalmologist or other eye or vision care professional can use the simulator to compare the performance of lenses of different design. In this case, the observer may be young enough to be able to accommodate. Therefore, the observer's eye will focus on the correct image by accommodation rather than by the brain restoring the image by image evaluation. An optical professional can prevent this. For example, the subject can concentrate on letters, symbols, or images 78 on the fovea window 26 so that they are readable and in focus. This causes the accommodation mechanism to focus on the anterior surface of fovea window 26 and, therefore, acquires any image as it appears on this location. In other words, the subject will "see" with the IOL.

The procedure described above assumes that all geometrical constants of the patient's eye are known. Of course, they can be measured and the procedure as described above can then be performed. Alternatively, the apparatus and method of the invention can be used for screening subjects to ascertain whether their brains are capable of the image evaluation required to use a bifocal IOL. For this purpose it is not necessary, at least initially, to use the exact dimensions of the subject's eye. It will be sufficient to use the measurements of the standard eye and use the appropriate IOL 10 for this eye. What appears on fovea window 26 is an image which is defocused to a degree that is typical. If the subject can handle this situation, then this is an indication that he will be able to handle a bifocal IOL unless his eye dimensions deviate considerably from normal. Also, considering that the dimensions of the eye will change with advancing age, it may be advantageous to wait with obtaining the patient's eye dimensions until near the time when cataract surgery is required.

With this approach the screening procedure becomes fairly simple, a matter of a few minutes. However, the ophthalmologist may decide to take the time to record the fovea window settings. Since the fovea projector performs a 1:1 image on the patient's fovea a change in the setting of the fovea window, required by the subject to see well, indicates that the subject's eye geometry has changed as well. Changes from year to year are to be expected, however, extreme changes may indicate the onset of glaucoma.

The methods and apparatus of the invention can also be used for research and pedagological purposes. For example, the image from the fovea window can be projected onto a screen, wall or other surface. This can be useful for teaching vision care professionals or others aspects of the methods and apparatus, aspects of the design and manufacture of intraocular lenses, and the like. Furthermore, the image from the fovea window can be projected onto film, a video camera, or like devices for storage and analysis of the image. With an appropriate lens or prism arrangement, such projection can occur simultaneously with a subject viewing the image at the fovea projector eye piece. Projection of an image from the fovea window into the eye of a nonhuman animal allows pharmacological, experimental, or clinical studies of image detection and vision.

The invention has been described with reference to various specific and preferred embodiments and techniques. However, it should be understood that many variations and modifications may be made while remaining within the spirit and scope of the invention.

What is claimed is:

1. An apparatus for evaluating vision through an intraocular lens comprising:

a basin with a chamber for holding liquid;

a cornea allowing light to enter the basin;

an intraocular lens holder positioned in the chamber; and a fovea window allowing light to exit the basin wherein the cornea, the intraocular lens holder and the fovea window are in a collinear array with the intraocular lens holder positioned between the fovea window and the cornea.

2. The apparatus of claim 1 further comprising an iris cap mounted between the intraocular lens holder and the cornea, the iris cap defining a central aperture.

3. The apparatus of claim 1 further comprising a fovea projector including an objective lens, and an eyepiece oriented such that light that entering through the fovea window is detectable at the eyepiece.

4. The apparatus of claim 1 further comprising an intraocular lens in the intraocular lens holder and fluid in the basin.

5. The apparatus of claim 1 further comprising a bifocal intraocular lens mounted to the intraocular lens holder.

6. The apparatus of claim 1 further comprising a moveable bellows mounted to the basin and the fovea window, wherein the fovea window is movably mounted relative to the basin.

7. The apparatus of claim 1 further comprising a control mechanism, wherein the intraocular lens holder is mounted to the control mechanism to move the intraocular lens holder relative to the basin on an x-axis, a z-axis and about an angle theta.

8. The apparatus of claim 1 wherein the basin, cornea, and intraocular lens holder are components of a human eye model that is mounted on a fovea projector; and further comprising a target box with a moveable target; wherein the target is in the field of view from the eyepiece of the fovea projector through the human eye model.

9. A method for evaluating a subject's vision through an intraocular lens comprising the steps of:

providing an intraocular lens that projects an image of a target onto a fovea window;

viewing symbols on the fovea window through the fovea window; and viewing the target through the intraocular lens and the fovea window.

10. The method of claim 9 further comprising the step of viewing an additional target.

11. The method of claim 9 further comprising the step of changing the position of the intraocular lens relative to the fovea window.

12. The method of claim 9 wherein the intraocular lens projects more than one image of the target on the fovea window.

13. The method of claim 9 further comprising the step of replacing the intraocular lens with an intraocular lens of a different design.

14. A method for evaluating vision through an intraocular lens comprising the steps of:

providing a human eye model including an intraocular lens and a fluid filled basin;

positioning a bifocal intraocular lens inside the basin;

passing light from a first target through the intraocular lens;

passing light from a target at a different distance from the intraocular lens through the intraocular lens; and passing the light from the first target and from the second target from the basin after passing through the intraocular lens.

\* \* \* \* \*